(12) United States Patent
Dubois

(10) Patent No.: US 8,697,401 B2
(45) Date of Patent: Apr. 15, 2014

(54) METHOD FOR SYNTHESIZING AN ω-AMINO ACID OR ESTER FROM A MONOUNSATURATED FATTY ACID OR ESTER

(75) Inventor: Jean-Luc Dubois, Millery (FR)

(73) Assignee: Arkema France, Colombes (FR)

( * ) Notice: Subject to any disclaimer, the term of this patent is extended or adjusted under 35 U.S.C. 154(b) by 404 days.

(21) Appl. No.: 13/131,748

(22) PCT Filed: Feb. 5, 2010

(86) PCT No.: PCT/FR2010/050186
§ 371 (c)(1),
(2), (4) Date: Jul. 1, 2011

(87) PCT Pub. No.: WO2010/089512
PCT Pub. Date: Aug. 12, 2010

(65) Prior Publication Data
US 2011/0300590 A1    Dec. 8, 2011

(30) Foreign Application Priority Data

Feb. 5, 2009 (FR) .................................. 09 50704

(51) Int. Cl.
*C12P 13/00* (2006.01)
(52) U.S. Cl.
USPC ...................................................... 435/128
(58) Field of Classification Search
USPC ............................ 435/128; 560/155; 562/553
See application file for complete search history.

(56) References Cited

U.S. PATENT DOCUMENTS 3,974,196 A   8/1976 Nakamura

FOREIGN PATENT DOCUMENTS

| GB | 741739 | * 12/1955 |
| GB | 741739 A | 12/1955 |
| WO | 2008/104722 A | 9/2008 |

OTHER PUBLICATIONS

Ngo et al. (Metathesis of Unsaturated Fatty Acids: Synthesis of Long-Chain Unsaturated-α,ω-Dicarboxylic Acids, JAOCS, vol. 83, No. 7, 2006).*
Aharoni, S. (1997) "n-Nylons: Their Synthesis, Structure, and Properties" Ch. 2.9: 381-389.
Ravve, A. (1967) "Organic Chemistry of Macromolecules" Ch. 15: 279-290.
Pryde, E.H. et al. (1962) "Aldehydic Materials by the Ozonization of Vegetable Oils" Journal of the American Oil Chemists' Society, 39:496-500.
Throckmorton, P.E. et al. (1967) "Pilot Run, Plant Design and Cost Analysis for Reductive Ozonolysis of Methyl Soyate" Journal of the American Oil Chemists' Society, 49:643-648.
Perkins, R.B., et al. (1975) "Nylon-9 from Unsaturated Fatty Derivates: Preparation and Characterization" Journal of the American Oil Chemists' Society, 52:473-477.
Eschenfeldt, W. et al. (2003) "Transformation of Fatty Acids Catalyzed by Cytochrome P450 Monooxygenase Enzymes of *Candida tropicalis*" Applied and Environmental Microbiology, 69: 5992-5999.
Mol, J.C. (2004) "Catalytic Metathesis of Unsaturated Fatty Acid Esters and Oils" Topics in Catalysis, 27: 97-104.
Schaverien, C. (1986) "A Well-Characterized Highly Active, Lewis Acid Free Olefin Metathesis Catalyst" J. American Chemical Society, 108: 2771-2773.
Coutrier, J. et al. (1992) "A Cyclometalated Aryloxy(chloro)neopentylidenetungsten Complex: A Highly Active and Stereoselective Catalyst for he Metathesis of cis- and trans-2-Penten Norbornene, 1-Methyl-norbonene, and Ethyl Oleate" Angew. Chem. 31: 628-631.
Schwab, P. (1995) "A Series of Well-Defined Metathesis Catalysts-Synthesis of [RuCl2(=CHR')(PR3)2] and its Reactions" Angew. Chem. 34: 2039-2041.
Scholl, M. et al. (1999) "Synthesis and Activity of a New Generation of Ruthenium-Based Olefin Metathesis Catalysts Coordinated with 1,3-Dimesityl-4, 5-dihydroimidazol-2-ylidene Ligands" Organic Letters 1: 953-956.
Drawert, F. et al. (1972) "Formation of 9-oxo-nonanoic acid methyl ester and 12-oxo-dodecanoate from Linoleic and and Linolsauremethylester and 9-oxo-nonanoic acid from Sunflower Oil by Irradiation with 6 Mrad" Chem. Mikrobiol. Technol. Lebensm. 1: 158-159. English Abstract provided.
Zhang, G. et al. (1994) "Study on Oxidation of Benzilic Ethers, Oximes and 1,2-diols by Ammonium Chlorochromate" Chinese Chemical Letters, 5: 105-108.
Ngo, H. et al. (2006) "Metathesis of Unsaturated Fatty Acids: Synthesis of Long-Chain Unsaturated-α, ω-Dicarboxylic Acids" JAOCS, 83:629-634.
International Search Report received in PCT/FR2010/050186. Mailed Jun. 14, 2010.

* cited by examiner

Primary Examiner — Wu-Cheng Winston Shen
Assistant Examiner — Blaine G Doletski
(74) Attorney, Agent, or Firm — Smith, Gambrell & Russell, LLP

(57) ABSTRACT

The invention relates to a method for synthesizing ω-aminoalkanoic acids or esters thereof from unsaturated natural fatty acids, passing through a monounsaturated dinitrile intermediate compound. The method of the invention is simple to carry out and, compared to other known methods, avoids the environmental constraints and economic disadvantages due to reaction by-products.

11 Claims, No Drawings

METHOD FOR SYNTHESIZING AN ω-AMINO ACID OR ESTER FROM A MONOUNSATURATED FATTY ACID OR ESTER

The invention is targeted at a process for the synthesis of ω-aminoalkanoic acids or their esters from natural monounsaturated fatty acids passing through an intermediate compound of monounsaturated dinitrile type.

The polyamides industry uses a whole range of monomers consisting of long-chain ω-amino acids, normally known as Nylon, characterized by the length of methylene chain $(-CH_2-)_n$ separating two amide functional groups —CO—NH—. Thus it is that Nylon 6, Nylon 6,6, Nylon 6,10, Nylon 7, Nylon 8, Nylon 9, Nylon 11, Nylon 13, and the like, are known.

These monomers are, for example, manufactured by a chemical synthesis route using in particular, as starting material, $C_2$ to $C_4$ olefins, cycloalkanes or benzene but also castor oil (Nylon 11), erucic or lesquerolic oil (Nylon 13), and the like.

Current developments with regard to the environment are resulting in the use of natural starting materials originating from a renewal source being favored in the fields of energy and chemistry. This is the reason why some studies have been taken up to develop, industrially, processes using fatty acids/esters as starting material in the manufacture of these monomers.

This type of approach has only a few industrial examples. One of the rare examples of an industrial process using a fatty acid as starting material is that of the manufacture, from the ricinoleic acid extracted from castor oil, of 11-aminoundecanoic acid, which forms the basis of the synthesis of Rilsan 11®. This process is described in the work "Les Procédés de Pétrochimie" [Petrochemical Processes] by A. Chauvel et al., which appeared in Editions Technip (1986). 11-Aminoundecanoic acid is obtained in several stages. The first consists of a methanolysis of castor oil in a basic medium, producing methyl ricinoleate, which is subsequently subjected to a pyrolysis in order to obtain, on the one hand, heptanaldehyde and, on the other hand, methyl undecylenate. The latter is converted to the acid form by hydrolysis. Subsequently, the acid formed is subjected to a hydrobromination to give the ω-brominated acid, which is converted by amination to 11-aminoundecanoic acid.

The main research studies have related to the synthesis of 9-aminononanoic acid, which is the precursor of Nylon 9, from oleic acid of natural origin.

As regards this specific monomer, mention may be made of the work "n-Nylons, Their Synthesis, Structure and Properties", 1997, published by J. Wiley and Sons, chapter 2.9 (pages 381 to 389) of which is devoted to Nylon 9. This article summarizes the preparations and studies carried out with regard to the subject. Mention is made therein, on page 381, of the process developed in the former Soviet Union which has resulted in the commercialization of Pelargon®. Mention is also made therein, on page 384, of a process developed in Japan which uses oleic acid originating from soybean oil as starting material. The corresponding description makes reference to the work by A. Ravve "Organic Chemistry of Macromolecules" (1967) Marcel Dekker, Inc., part 15 of which is devoted to polyamides and which mentions, on page 279, the existence of such a process.

In order to be fully informed with regard to the state of the art on this subject, mention should be made of the numerous papers published by E. H. Pryde et al. between 1962 and 1975 in the Journal of the American Oil Chemists' Society—"Aldehydic Materials by the Ozonization of Vegetable Oils", Vol. 39, pages 496-500; "Pilot Run, Plant Design and Cost Analysis for Reductive Ozonolysis of Methyl Soyate", Vol. 49, pages 643-648, and R. B. Perkins et al., "Nylon-9 from Unsaturated Fatty Derivatives: Preparation and Characterization", JAOCS, Vol. 52, pages 473-477. It should be noted that the first of these papers also makes reference, on page 498, to previous studies carried out by the Japanese authors H. Otsuki and H. Funahashi.

To summarize this part of the state of the art targeted at this type of synthesis of "Nylon 9" from vegetable oils, a description may be given of the following simplified reaction mechanism applied to the oleic ester extracted from the oils by methanolysis:

Reductive Ozonolysis

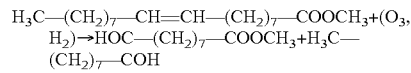

Reductive Amination

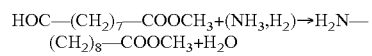

Hydrolysis

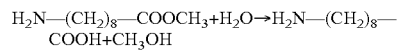

However, this route, which is very attractive from the reaction viewpoint, exhibits a significant economic drawback consisting of the production, during the first stage, of a long-chain aldehyde (9 carbon atoms in total) which in practice cannot be recovered in value, in particular in the polymer industry relating to polyamides.

The UK patent No. 741 739 describes, for its part, the synthesis of this same acid from oleic acid but using the oleonitrile route. The simplified reaction scheme for this process is as follows. An analogous route is mentioned in the abovementioned paper by R. B. Perkins et al., p. 475.

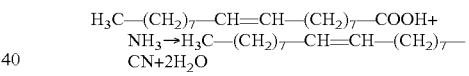

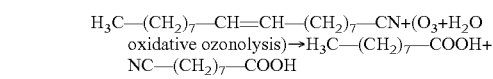

This synthesis results in pelargonic acid $H_3C-(CH_2)_7-$COOH as byproduct.

The present invention is targeted at providing a novel process for synthesizing a whole range of ω-amino-alkanoic acids or their esters from natural monounsaturated fatty acids.

The problem is thus that of finding a process for the synthesis of various ω-amino acids of formula $H_2N-(CH_2)_n-$COOH in which n is between 3 and 14 (and of their polymers), starting from very widely accessible and therefore inexpensive renewable starting materials, which is simple to carry out while avoiding, on the one hand, the environmental constraints mentioned above and, on the other hand, the economic handicaps due to the byproducts from the reactions.

The solution provided consists in working from starting materials consisting of natural long-chain unsaturated fatty acids comprising, if appropriate, a hydroxyl functional group, in converting them, in a first stage, into monounsaturated dinitriles and in then subsequently, in a second stage, "reinserting" a carboxylic acid functional group into the final product by an action on the double bond of the monounsaturated dinitrile which brings about cleavage of the dinitrile molecule, either by means of oxidative cleavage or by a cross metathesis reaction with a compound of acrylate type.

The term "natural fatty acid" is understood to mean an acid resulting from the plant or animal milieu, including algae, more generally from the plant kingdom, and thus renewable. This acid, composed of at least 10 and preferably of at least 14 carbon atoms per molecule, will comprise at least one olefinic unsaturation, the location of which in the x position with respect to the acid group (delta x) will determine the formula of the final ω-amino acid. In addition, this natural fatty acid can, if appropriate, comprise a hydroxyl functional group.

Mention may be made, as examples of such acids, of the $C_{10}$ acids obtusilic (cis-4-decanoic) acid and caproleic (cis-9-decenoic) acid, the $C_{12}$ acids lauroleic (cis-5-dedecenoic) acid and linderic (cis-4-dodecenoic) acid, the $C_{14}$ acids myristoleic (cis-9-tetradecenoic) acid, physeteric (cis-5-tetradecenoic) acid and tsuzuic (cis-4-tetradecenoic) acid, the $C_{16}$ acid palmitoleic (cis-9-hexadecenoic) acid, the $C_{18}$ acids oleic (cis-9-octadecenoic) acid, elaidic (trans-9-octa-decenoic) acid, petroselinic (cis-6-octadecenoic) acid, vaccenic (cis-11-octadecenoic) acid and ricinoleic (12-hydroxy-cis-9-octadecenoic) acid, the $C_{20}$ acids, gadoleic (cis-9-eicosenoic) acid, gondoic (cis-11-eicosenoic), cis-5-eicosenoic acid and lesquerolic (14-hydroxy-cis-11-eicosenoic) acid, and the $C_{22}$ acids cetoleic (cis-11-docosenoic) acid and eruric (cis-13-dodecosenoic) acid.

The process can also be applied to polyunsaturated acids, such as linoleic (cis,cis-9,12-octadecadienoic and cis,trans-9,11-octadecadienoic) acids, α-linoleic (cis,cis,cis-9,12,15-octadecatrienoic) acid or α-eleostearic (cis,trans,trans-9,11,13-octadeca-trienoic) acid, but with the disadvantage of multiplying the byproducts.

These various acids result from the vegetable oils extracted from various oleaginous plants, such as sunflower, rape, castor oil plant, bladderpod, olive, soya, palm tree, avocado, sea buckthorn, coriander, celery, dill, carrot, fennel, *Limnanthes alba* (meadowfoam), safflower or camelina.

They also result from the terrestrial or marine animal world and, in the latter case, both in the form of fish or mammals, on the one hand, and of algae, on the other hand. They are in general fats originating from ruminants, from fish, such as cod, or from marine mammals, such as whales or dolphins.

The invention is targeted at a process for the synthesis of an ω-amino acid (ester) of formula $ROOC-(CH_2)_q-CH_2-NH_2$, in which R is H or an alkyl radical comprising from 1 to 4 carbon atoms and q is an integral index equal either to p or to p+2 or to n or n+2, of between 2 and 15, starting from a monounsaturated fatty acid (ester) of formula $R_1-CH=CH-(CH_2)_p-COOR_2$, in which $R_1$ is either H or an alkyl radical comprising from 4 to 14 carbon atoms and, if appropriate, a hydroxyl functional group, $R_2$ is H or an alkyl radical comprising from 1 to 4 carbon atoms and p is an integral index of between 2 and 11, comprising an ammoniation reaction stage resulting in the conversion of the carbonyl functional group to a nitrile functional group, characterized in that:

in a first stage, the unsaturated fatty acid/ester is converted to an unsaturated dinitrile of formula $NC-(CH_2)_p-CH=CH-(CH_2)_n-CN$, in which n is an integer of between 3 and 13, depending on the nature of the $R_1$ radical, in two successive stages, the first stage being either a homometathesis of the fatty acid, resulting in the symmetrical unsaturated diacid of formula $R_2OOC-(CH_2)_p-CH=CH-(CH_2)_p-COOR_2$, or a fermentation of this acid/ester, resulting in an unsaturated diacid of formula $HOOC-(CH_2)_p-CH=CH-(CH_2)_n-COOH$ (the fermentation will give diacids—the alcohol is consumed), and the second stage being an ammoniation of the acids, then, in a second stage, this unsaturated dinitrile is converted to an acid/ester nitrile of formula $R_3OOC-[CH=CH]_x-(CH_2)_{p,n}-CN$, in which $R_3$ is H or an alkyl radical comprising from 1 to 4 carbon atoms, x is 0 or 1 and "p,n" means that the index is either p or n, according to the route chosen during the first stage, which conversion is carried out either by oxidative cleavage of unsaturated dinitrile or by a cross metathesis reaction of the unsaturated dinitrile with an acrylate of formula $CH_2=CH-COOR_3$, and, in a third stage, the acid/ester nitrile is hydrogenated to give an Ω-amino acid (ester) of formula $R_3OOC-(CH_2)_q-CH_2NH_2$.

In an alternative form of the process employing the homometathesis route during the first stage, it is possible to invert the order of the stages of ammoniation, resulting in the nitrile, and of metathesis, which is applied here to the fatty nitrile in order to change to the dinitrile.

The reaction process of the general case is then as follows:
1) First Stage:
Either Homometathesis

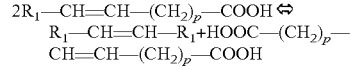

Or Fermentation

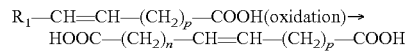

then

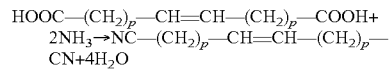

or

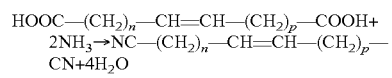

2) Second Stage:
First Alternative Form (Oxidative Cleavage)

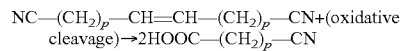

or

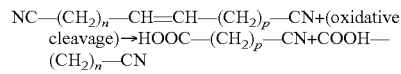

Second Alternative Form (Cross Metathesis)

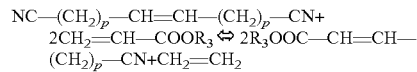

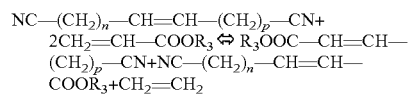

3) Third Stage:
First Alternative Form After Oxidative Cleavage

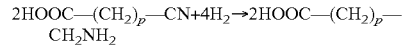

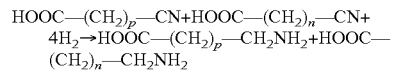

Second Alternative Form after Metathesis

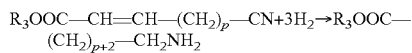

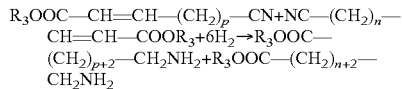

In the preceding reaction scheme, as for the following reaction schemes, when it is indicated that the reaction involves the acid form of the compound, it can just as easily apply to its ester form.

These various mechanisms are illustrated by the schematic diagram (scheme 1) which appears below in the description.

When applied to oleic acid, for which n is equal to p, $R_3OOC-(CH_2)_9-CH_2NH_2$ is obtained by the cross metathesis route and $R_3OOC-(CH_2)_7-CH_2NH_2$ is obtained by the oxidative cleavage route.

When applied to an acid, the double bond of which is not located at the center of the molecule, such as palmitoleic acid, the processes become i) 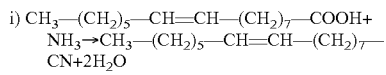

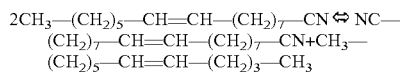

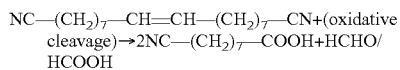

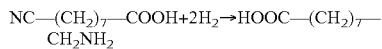

ii) 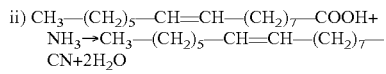

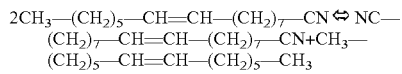

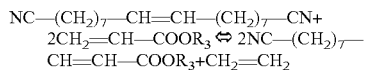

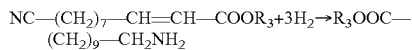

iii) 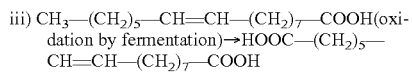

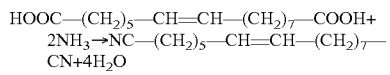

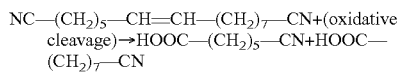

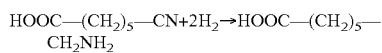

iv) 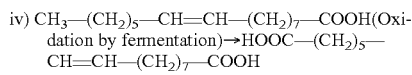

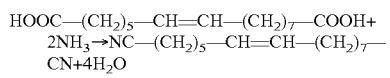

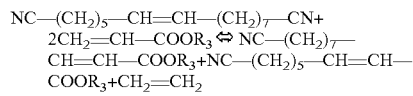

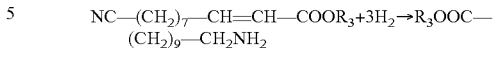

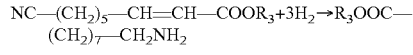

The only "byproducts" formed are a long-chain α-olefin, if appropriate comprising a hydroxyl functional group, and formaldehyde or formic acid.

In a first alternative embodiment of the process, during the first stage, the homometathesis of the fatty acid/ester of formula $R_1-CH=CH-(CH_2)_p-COOR_2$ is first of all carried out and then the ammoniation of the fatty diacids/diesters obtained is carried out in order to obtain a fatty dinitrile, then, in a second stage, this dinitrile is converted to an acid nitrile of formula $HOOC-(CH_2)_p-CN$ by oxidative cleavage and, finally, in a third stage, the nitrile functional group is reduced by hydrogenation to give an amine functional group, in order to obtain the compound of formula $ROOC-(CH_2)_p-CH_2NH_2$.

In a second alternative embodiment of the process, during the first stage, the homometathesis of the fatty acid (ester) of formula $R_1-CH=CH-(CH_2)_p-COOR_2$ is first of all carried out, in order to obtain the diacid/ester of formula $R_2OOC-(CH_2)_p-CH=CH-(CH_2)_p-COOR_2$, and then the ammoniation of the fatty diacids/diesters obtained is carried out, in order to obtain a fatty dinitrile, then, in a second stage, this dinitrile is converted to an acid/ester nitrile of formula $R_3OOC-[CH=CH]-(CH_2)_p-CN$ by cross metathesis with the alkyl acrylate $CH_2=CH-COOR_3$ and, finally, in a third stage, the double bond and the nitrile functional group are simultaneously reduced by hydrogenation to give an amine, in order to obtain the compound of formula $R_3OOC-(CH_2)_{p+2}-CH_2NH_2$.

In a third alternative embodiment of the process, during the first stage, the ammoniation of the fatty acid (ester) of formula $R_1-CH=CH-(CH_2)_p-COOR_2$ is first of all carried out, resulting in the corresponding nitrile, and then the conversion by homometathesis of the nitrile to give an unsaturated fatty dinitrile of formula $NC-(CH_2)_p-CH=CH-(CH_2)_p-CN$ is carried out, then this dinitrile is converted to an acid nitrile of formula $HOOC-(CH_2)_p-CN$ by oxidative cleavage and, finally, in a third stage, the nitrile functional group is reduced to an amine functional group by hydrogenation, in order to obtain the compound of formula $HOOC-(CH_2)_p-CH_2NH_2$.

In a fourth alternative embodiment of the process, during the first stage, the ammoniation of the fatty acid (ester) of formula $R_1-CH=CH-(CH_2)_p-COOR_2$ is first of all carried out, resulting in the corresponding nitrile, and then the conversion by homometathesis of the nitrile to give an unsaturated fatty dinitrile of formula $NC-(CH_2)_p-CH=CH-(CH_2)_p-CN$ is carried out, then, in a second stage, this dinitrile is converted to an ester nitrile of formula $R_3OOC-[CH=CH]-(CH_2)_p-CN$ by cross metathesis with the alkyl acrylate $CH_2=CH-COOR_3$ and, finally, in a third stage, the double bond and the nitrile functional group are simultaneously reduced by hydrogenation to give an amine, in order to obtain the compound of formula $R_3OOC-(CH_2)_{p+2}-CH_2NH_2$.

In a fifth alternative embodiment of the process, during the first stage, the oxidation by fermentation of the fatty acid/ester of formula $R_1-CH=CH-(CH_2)_p-COOR_2$ is first of all carried out, in order to obtain the diacid/ester of formula $HOOC—(CH_2)_p—CH=CH—(CH_2)_n—COOR_2$, and then the ammoniation of the fatty diacids/diesters obtained is carried out, in order to obtain a fatty dinitrile of formula $NC—(CH_2)_p—CH=CH—(CH_2)_n—CN$, then, in a second stage, this dinitrile is converted to a mixture of two acid nitriles of formulae $HOOC—(CH_2)_p—CN$ and $HOOC—(CH_2)_n—CN$ by oxidative cleavage and, finally, in a third stage, the nitrile functional group is reduced by hydrogenation to an amine functional group, in order to obtain a mixture of compounds of formulae $HOOC—(CH_2)_p—CH_2NH_2$ and $HOOC—(CH_2)_n—CH_2NH_2$.

In a sixth alternative embodiment of the process, during the first stage, the oxidation by fermentation of the fatty acid/ester of formula $R_1—CH=CH—(CH_2)_p—COOR_2$ is first of all carried out, in order to obtain the diacid/ester of formula $HOOC—(CH_2)_p—CH=CH—(CH_2)_n—COOR_2$, and then the ammoniation of the fatty diacids/diesters obtained is carried out, in order to obtain a fatty dinitrile of formula $NC—(CH_2)_p—CH=CH—(CH_2)_n—CN$, then, in a second stage, this dinitrile is converted to a mixture of two acid/ester nitriles of formulae $R_3OOC—[CH=CH]—(CH_2)_p—CN$ and $R_3OOC—[CH=CH]—(CH_2)_n—CN$ by cross metathesis with the alkyl acrylate $CH_2=CH—COOR_3$ and, finally, in a third stage, the double bond and the nitrile functional group are simultaneously reduced by hydrogenation to give an amine, in order to obtain a mixture of compounds of formulae $R_3OOC—(CH_2)_{p+2}—CH_2NH_2$ and $R_3OOC—(CH_2)_{n+2}CH_2NH_2$.

The operating conditions of the various reactions involved are known and are described in the state of the art.

The reaction scheme for the synthesis of the nitriles starting from the acids can be summarized in the following way:

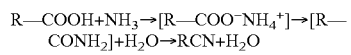
$R—COOH+NH_3 \rightarrow [R—COO^-NH_4^+] \rightarrow [R—CONH_2]+H_2O \rightarrow RCN+H_2O$ The process can be carried out batchwise in the liquid or gas phase or continuously in the gas phase. The reaction is carried out at a high temperature >250° C. and in the presence of a catalyst which is generally a metal oxide and most frequently zinc oxide. The continuous removal of the water formed while moreover entraining the unreacted ammonia makes possible rapid completion of the reaction.

When the process employs a stage of oxidation by fermentation, use is made of a microorganism, such as a bacterium, a fungus or a yeast, which makes possible the oxidation of the fatty acid or ester of the feedstock. Use will preferably be made of microorganisms comprising enzymes of Oxygenase type capable of oxidizing the feedstock with the formation of a trivalent functional group of acid —COOH or ester —COOR type.

This fermentation can, for example, be carried out in the presence of a *Candida tropicalis* strain comprising cytochrome P450 monooxygenase enzymes, such as those described in the publication by W. H. Eschenfeldt et al., "Transformation of Fatty Acids Catalyzed by Cytochrome P450 Monooxygenase Enzymes of *Candida tropicalis*", which appeared in Applied and Environmental Microbiology, October 2003, pp. 5992-5999, and patents FR 2 445 374, U.S. Pat. No. 4,474,882, U.S. Pat. No. 3,823,070, U.S. Pat. No. 3,912,586, U.S. Pat. No. 6,660,505, U.S. Pat. No. 6,569,670 and U.S. Pat. No. 6,254,466.

The metathesis reactions have been known for a long time, even if their industrial applications are relatively limited. Reference may be made, with regard to their use in the conversion of fatty acids (esters), to the paper by J. C. Mol, "Catalytic Metathesis of Unsaturated Fatty Acid Esters and Oil", which appeared in Tropics in Catalysis, Vol. 27, Nos. 1-4, February 2004 (Plenum Publishing).

The catalysis of the metathesis reaction has formed the subject of a great many studies and the development of sophisticated catalytic systems. Mention may be made, for example, of the tungsten complexes developed by Schrock et al., J. Am. Chem. Soc., 108 (1986), 2771, or Basset et al., Angew. Chem., Ed. Engl., 31 (1992), 628. More recently, "Grubbs" catalysts, which are ruthenium-benzylidene complexes, have appeared (Grubbs et al., Angew. Chem., Ed. Engl., 34 (1995), 2039, and Organic Lett., 1 (1999), 953). These relate to homogeneous catalysis. Heterogeneous catalysts have also been developed which are based on metals, such as rhenium, molybdenum and tungsten, deposited on alumina or silica. Finally, studies have been carried out on the preparation of immobilized catalysts, that is to say catalysts whose active principle is that of a homogeneous catalyst, in particular ruthenium-carbene complexes, but which is immobilized on an inactive support. The object of these studies is to increase the selectivity of the cross metathesis reaction with regard to the side reactions, such as "homometathesis" between the reactants brought together. They relate not only to the structure of the catalysts but also to the effect of the reaction medium and the additives which may be introduced.

Any active and selective metathesis catalyst can be used in the process of the invention. However, use will preferably be made of ruthenium-based catalysts.

The cross metathesis reaction with the compound of acrylate type is carried out under conditions which are fully known. The reaction temperature is between 20 and 100° C. at a pressure of approximately atmospheric pressure (1 to 10 bar) in the presence of a ruthenium-based catalyst, for example. The reaction time is chosen according to the reactants employed and in order to reach as close as possible to the equilibrium of the reaction.

The ruthenium catalysts are preferably chosen from the charged or uncharged catalysts of general formula:

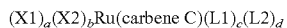
$(X1)_a(X2)_b Ru(carbene\ C)(L1)_c(L2)_d$ in which:
- a, b, c and d are integers with a and b equal to 0, 1 or 2 and c and d equal to 0, 1, 2, 3 or 4;
- X1 and X2, which are identical or different, each represent a charged or uncharged and mono- or multichelating ligand; mention may be made, by way of examples, of halides, sulfate, carbonate, carboxylates, alkoxides, phenates, amides, tosylate, hexafluoro-phosphate, tetrafluoroborate, bistriflylamide, tetra-phenylborate and derivatives. X1 or X2 can be bonded to Y1 or Y2 or to the (carbene C) so as to form a bidentate ligand (or chelate) on the ruthenium; and
- L1 and L2, which are identical or different, are electron-donating ligands, such as phosphine, phosphite, phosphonite, phosphinite, arsine, stilbene, an olefin or an aromatic, a carbonyl compound, an ether, an alcohol, an amine, a pyridine or a derivative, an imine, a thioether or a heterocyclic carbene,
- L1 or L2 can be bonded to the "carbene C" so as to form a bidentate ligand or chelate, The "carbene C" can be represented by the general formula: $C\_(R1)\_(R2)$ for which R1 and R2 are identical or different, such as hydrogen or any other saturated or unsaturated, cyclic, branched or linear, or aromatic hydrocarbonyl group. Mention may be made, by way of examples, of alkylidene or cumulene complexes of ruthenium, such as vinylidenes $Ru=C=CHR$ or allenylidenes $Ru=C=C=CR1R2$ or indenylidenes.

A functional group which makes it possible to improve the retention of the ruthenium complex in the ionic liquid can be grafted to at least one of the ligands X1, X2, L1 or L2 or to the carbene C. This functional group can be charged or uncharged, such as, preferably, an ester, an ether, a thiol, an acid, an alcohol, an amine, a nitrogenous heterocycle, a sulfonate, a carboxylate, a quaternary ammonium, a guanidinium, a quaternary phosphonium, a pyridinium, an imidazolium, a morpholinium or a sulfonium.

The oxidative cleavage reaction on the double bond, which results in the formation of the acid functional group on the two carbons of the double bond, is also known per se.

It can be carried out by means of a strong oxidizing agent, such as $KMnO_4$ in a concentrated form and with heating, as is described in "Organic Chemistry" by L. G. Wade Jr., $5^{th}$ edition, Chapter 8, Reactions of Alkenes.

The oxidative cleavage can be carried out with aqueous hydrogen peroxide solution, as described in the patent GB 743 491. The paper by F. Drawert et al. in Chem. Mikrobiol. Technol. Lebensm., 1, 158-159 (1972), describes an alternative route by irradiation of sunflower oil. Moreover, the paper by G. S. Zhang et al. in Chinese Chemical Letters, Vol. 5, No. 2, pp. 105-108, 1994, indicates that it is possible to carry out the oxidative cleavage starting from the corresponding diol of oleic acid (see Entry 29 of the table). This oxidative cleavage is carried out using ammonium chlorochromate as oxidizing agent. For its part, the diol is obtained by epoxidation of oleic acid, followed by hydrolysis of the epoxy bridge.

It can be carried out with other oxidizing agents, such as aqueous hydrogen peroxide solution and more particularly ozone.

Numerous studies have been carried out on the use of ozone as oxidizing agent. Furthermore, it is mentioned, in the abovementioned Angew. Chem. work, that the oxidative cleavage of oleic acid to perlargonic acid and azelaic acid is the most important industrial application of ozonolysis.

The U.S. Pat. No. 2,813,113 describes in particular a process for the oxidative ozonolysis of a fatty acid, such as oleic acid, which consists, in a first stage, in treating the acid with oxygen in combination with ozone, in order to form ozonides, and then, in a second stage, in oxidizing the latter compounds with oxygen. Use is not made, in this type of reaction, of compounds which block the oxidation process at the stage of the ketones or aldehydes, in what is known as reductive ozonolysis, which has more recently formed the subject of important studies.

The stage of synthesis of the fatty ω-amino acids (esters) from the fatty acid nitriles consists of a conventional hydrogenation. There are many catalysts but use is preferably made of Raney nickels and cobalts. In order to promote the formation of the primary amine, the hydrogenation is carried out with an ammonia partial pressure. Finally, the reduction of the nitrile functional group to give a primary amine is well known to a person skilled in the art.

In the process of the invention, the fatty acid can be treated either in its acid form or in its ester form. The perfectly commonplace change from one form to the other, by methanolysis, esterification or hydrolysis, does not constitute a chemical conversion within the meaning of the process.

All the mechanisms described below illustrate, in order to facilitate the account, the synthesis of the acids. However, the metathesis is also effective with an ester and even more effective, the medium generally being more anhydrous. In the same way, the schemes illustrate reactions with the cis isomer of the acids (or esters); the mechanisms are applicable equally well to the trans isomers.

The reaction mechanism of this reaction is illustrated in scheme 1 below.

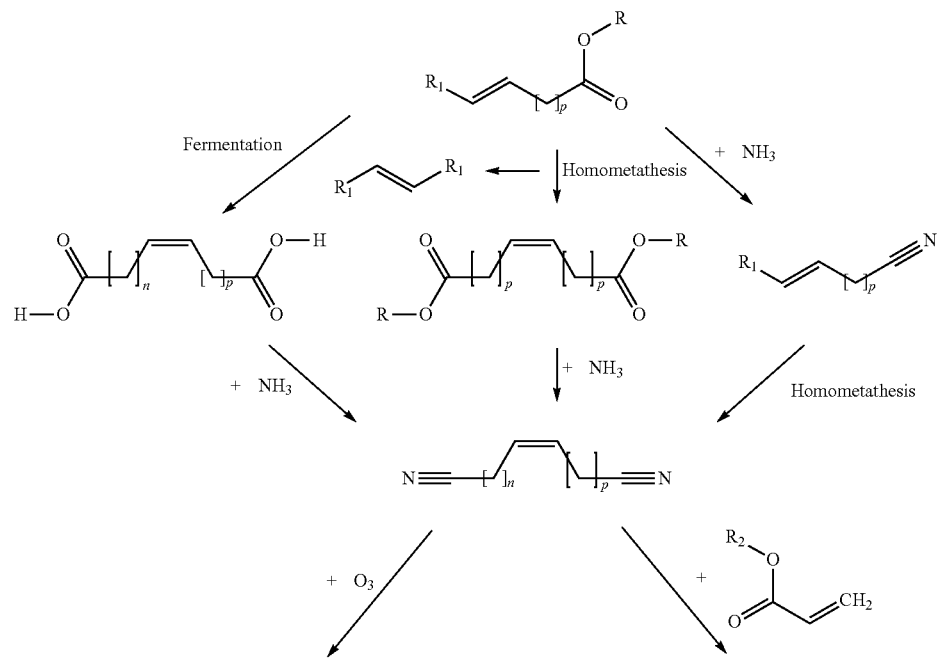

Scheme 1

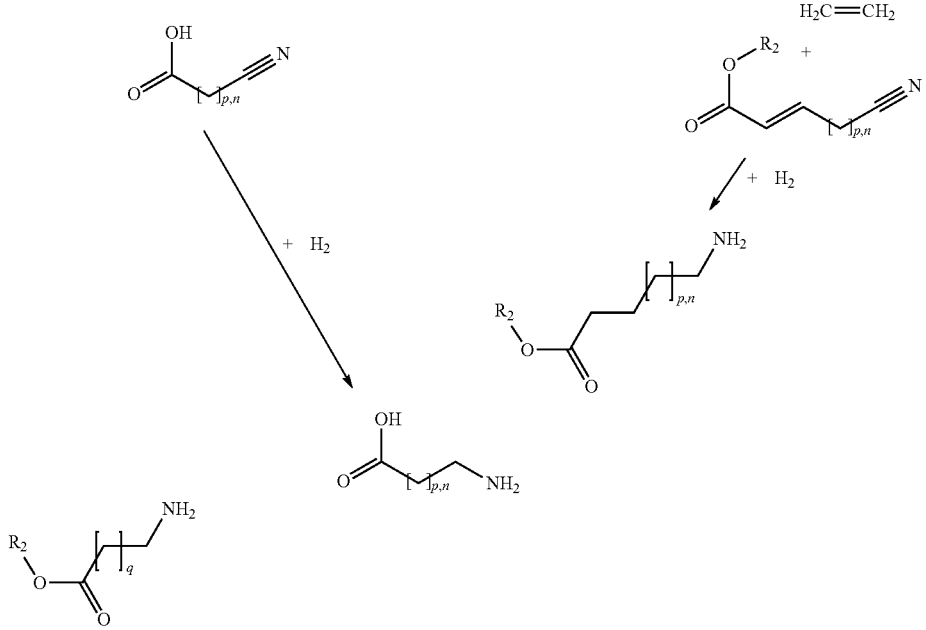

$q$ = n or p via ozonolysis and n or p plus 2 via cross metathesis

The invention additionally relates to the amino acid or amino ester of renewable origin of general formula $NH_2$—$(CH_2)_q$—COOR, R being either H or an alkyl radical comprising from 1 to 4 carbon atoms.

The term "amino acids or amino esters of renewable origin" is understood to mean the amino acids or amino esters which comprise carbon of renewable origin.

By employing the process of the invention, it will be possible to synthesize the whole range of ω-amino acids from 4-aminotetranoic acid to 17-aminoheptadecanoic acid.

4-Aminotetranoic acid can be obtained from obtusilic, linderic and tsuzuic acids.

5-Aminopentanoic acid can be obtained from lauroleic, myristoleic, cis-5-eicosenoic and physiteric acids.

6-Aminohexanoic acid can be obtained from obtusilic, linderic, tsuzuic and petroselenic acids.

7-Aminoheptanoic acid can be obtained from lauroleic, palmitoleic, myristoleic, physiteric, cis-5-eicosenoic and vaccenic acids.

8-Aminooctanoic acid can be obtained from obtusilic, linderic and petroselenic acids.

9-Aminononanoic acid can be obtained from caproleic, lauroleic, myristoleic, physiteric, palmitoleic, oleic, elaidic, vaccenic, gadoleic, ricinoleic and erucic acids.

10-Aminodecanoic acid can be obtained from linderic and tsuzuic acids.

11-Aminoundecanoic acid can be obtained from caproleic, myristoleic, physiteric, palmitoleic, oleic, elaidic, vaccenic, ricinoleic, lesquerolic, gadoleic and erucic acids.

12-Aminododecanoic acid can be obtained from tsuzuic and petroselenic acids.

13-Aminotridecanoic acid can be obtained from vaccenic, gadoleic, lesquerolic and erucic acids.

14-Aminotetradecanoic acid can be obtained from petroselenic acid.

15-Aminopentadecanoic acid can be obtained from erucic and cis-5-eicosenoic acids.

17-Aminoheptadecanoic acid can be obtained from cis-5-eicosenic acid.

The invention is illustrated by the following examples.

Example 1

This example illustrates the first stage by fermentation of oleic acid, producing a diacid. In this example, use will be made of a yeast comprising at least one Oxygenase enzyme. The yeast will be cultured at pH=7 in a deionized water medium comprising sorbitol, trace elements, urea and oleic acid. The mixture will subsequently be sterilized at 120° C. for 15 minutes. A yeast strain will subsequently be inoculated in the culture medium. The culture will be maintained at 30° C. A sodium hydroxide solution will be continuously added in order to keep the medium at a pH of 7.0 to 7.5. After culturing for 48 hours, the unsaturated diacid will be recovered by extracting the diethyl ether. After removing the solvent by evaporation, crystals will be recovered which, after recrystallization, will have a melting point of 69° C., that is say equivalent to that described for 9-octa-decenedioic acid.

Example 2

This example illustrates the first stage carried out by homometathesis of oleic acid to give the symmetrical diacid of formula HOOC—$(CH_2)_7$—CH=CH—$(CH_2)$, —COOH 9-octa-decenedioic acid.

For this stage, use is made of metathesis catalyst obtained from Sigma Aldrich, catalogue reference 569747, corresponding to the following formula benzylidene[1,3-bis(2,4,6-trimethylphenyl)-2-imidazolidinylidene]dichloro(tricyclohexylphosphine)-ruthenium. This catalyst is known under the name of Grubbs catalyst, second generation, and Hoveyda-Grubbs catalyst, second generation.

In the experiment, 2.5 g of fatty acid ester of oleic acid (methyl oleate) are used. Tetradecane is used as internal standard. The reaction mixture is stirred at 50° C. and degassed with argon. The catalyst (1 mol %) is added to the solution, without addition of solvent. The samples of reaction products are analyzed by chromatography. After reacting for half an hour, a conversion of 98 mol % with a homometathesis yield of 100% is obtained.

Example 3

This example illustrates the ammoniation stage in which unsaturated diacid resulting from example 1 or 2 is converted to the unsaturated dinitrile.

The ammoniation reaction of 9-octadecenedioic acid to form the unsaturated dinitrile of formula NC—(CH$_2$)$_7$—CH=CH—(CH$_2$)$_7$—CN is carried out batchwise with introduction of ammonia in a large molar excess with respect to the acid and at a temperature of 300° C. at atmospheric pressure (in the gas phase) in the presence of a zinc oxide catalyst. The reactor is equipped with a condenser at 100° C. The ammonia is thus continuously injected for 6 hours. The continuous removal of the water formed entrains the excess ammonia and makes possible rapid completion of the reaction. The reaction yield is measured by chromatography and is 86%, with respect to the acid.

Example 4

This example illustrates the series of reactions: ammoniation of oleic acid, followed by one of homo-metathesis of the unsaturated nitrile thus obtained to give the unsaturated dinitrile.

The ammoniation reaction of oleic acid is carried out under conditions analogous to those of example 3 with 9-octadecenedioic acid.

The metathesis reaction is carried out at atmospheric pressure at 80° C. in the presence of a ruthenium-based catalyst [RuCl$_2$(=CHPh)(IMesH$_2$)(PCy$_3$)] using toluene as solvent. The yields are determined by chromatographic analysis. On completion of the reaction, 6 hours, the C$_{18}$ olefin is separated from the dinitrile by vacuum distillation.

Example 5

This example illustrates the oxidative cleavage of an unsaturated dinitrile (symmetrical or unsymmetrical) of formula NC—(CH$_2$)$_7$—CH=CH—(CH$_2$)$_7$—CN by oxidative ozonolysis to form the acid nitrile of formula CN—(CH$_2$)$_7$—COOH.

Ozone obtained by a Welsbach T-408 ozone generator is bubbled into 25 ml of pentane until a blue color is observed. The pentane solution is kept at −70° C. with an acetone/dry ice bath. 20 mg of dinitrile, dissolved in 5 ml of pentane cooled to 0° C., are added to the ozone solution. The excess ozone is subsequently removed and the blue color disappears. After 5 minutes, the pentane is evaporated with a stream of dry nitrogen. During this stage, the temperature of the solution is kept below 0° C. After evaporating the pentane, 3 ml of methanol cooled to −70° C. are added to the reactor while reheating it in order to make possible the dissolution of the ozonide.

Example 6

This example illustrates the cross metathesis reaction between the dinitrile of formula resulting from the stage of examples 2 and 4 with methyl acrylate in order to form the acid nitrile of formula NC—(CH$_2$)$_7$—CH=CH—COOH.

Use is made, for this stage, of a catalyst obtained from Sigma Aldrich, under the catalogue reference 569755, known as a Grubbs catalyst, second generation, and a Hoveyda-Grubbs catalyst, second generation. Its formula is as follows: [1,3-bis(2,4,6-trimethylphenyl)-2-imidazoldinylidene] dichloro(o-isopropoxyphenyl-methylene)ruthenium.

In the experiment, 2.5 g of fatty oleic dinitrile are mixed with an excess of methyl acrylate (molar ratio 10/1). Tetradecane is used as internal standard. The reaction mixture is stirred at 50° C. and degassed with argon. The catalyst (0.1 mol %) is added to the solution, without addition of solvent. The samples of reaction products are analyzed by chromatography. After reacting for half an hour, a conversion of 99 mol % with a cross metathesis yield of 99% is obtained.

Example 7

This example illustrates the hydrogenation of the double bond and of the nitrile functional group. The hydrogenation is carried out in the presence of a catalyst composed of a Raney nickel.

1 g of acid nitrile of formula NC—(CH$_2$)$_7$—COOH obtained in accordance with example 3 is esterified with methanol. 1 g of acid nitrile, 1.2 g of methanol, 1.2 g of benzene and a few drops of concentrated sulfuric acid are introduced into a reactor. The water/alcohol/benzene azeotrope is removed at the column top. Sulfuric acid is added continuously in order to keep the reaction progressing. Subsequently, the benzene and alcohol are flash distilled in order to recover the ester nitrile: 1.02 g.

The ester nitrile synthesized is placed in a stirred 15 ml autoclave and 2.5 g of 96% ethanol, 2.5 g of liquid ammonia and 0.125 g of Raney nickel catalyst comprising 3% by weight of cobalt are added thereto. The mixture is heated for 4 hours at 90° C. under 150 bar of hydrogen (total pressure 210 bar). The methyl ester is distilled under a vacuum of 0.5 mm of mercury. 0.97 g of a clear distillate is recovered. It comprises 90% of amino ester.

Example 8

This example illustrates the cross metathesis between oleonitrile and methyl acrylate, according to the following reaction scheme:

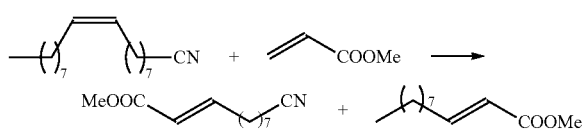

132 mg of 9-octadecenenitrile (0.5 mmol), 172 mg of methyl acrylate (2 mmol) and 10 ml of toluene distilled over sodium/benzophenone are charged to a 50 ml Schlenk tube purged with nitrogen. The mixture is heated to 100° C. and then, with magnetic stirring, 0.15 mg (2.5×10$^{-4}$ mmol) of Hoveyda-Grubbs catalyst, second generation, (Aldrich) dissolved in 2 ml of toluene is added with a syringe and a syringe driver over a period of 4 h. At the end of the addition, the mixture is left to react at 100° C. for 2 hours. The reaction mixture is analyzed by gas chromatography:
the conversion of the 9-octadecenenitrile is 93%,
the yield of methyl 10-cyano-2-decenoate is 80%.

The yield is expressed in number of moles of ester nitrile obtained with respect to the number of moles of C$_{11}$ nitrile involved.

What is claimed is:

1. A process for the synthesis of an ω-amino acid (ester) of formula ROOC—$(CH_2)_q$—$CH_2$—$NH_2$, in which R is H or an alkyl radical comprising from 1 to 4 carbon atoms and q is an integral index equal either to p or to p+2 or to n or n+2, of between 2 and 15, starting from a monounsaturated fatty acid (ester) of formula $R_1$—CH=CH—$(CH_2)_p$—$COOR_2$, in which $R_1$ is H, an alkyl radical comprising from 4 to 14 carbon atoms, or a hydroxyl functional group, $R_2$ is H or an alkyl radical comprising from 1 to 4 carbon atoms and p is an integral index of between 2 and 11, comprising an ammoniation reaction stage resulting in the conversion of the carbonyl functional group to a nitrile functional group, wherein:

in a first stage, the unsaturated fatty acid/ester is converted to an unsaturated dinitrile of formula NC—$(CH_2)_p$—CH=CH—$(CH_2)_n$—CN, in which n is an integer of between 3 and 13, depending on the nature of the $R_1$ radical, in two successive stages, the first stage being either a homometathesis of the fatty acid, resulting in the symmetrical unsaturated diacid of formula $R_2$OOC—$(CH_2)_p$—CH=CH—$(CH_2)_p$—$COOR_2$, or a fermentation of this acid/ester, resulting in an unsaturated diacid of formula HOOC—$(CH_2)_p$—CH=CH—$(CH_2)_n$—COOH, and the second stage being an ammoniation of the acids, then, in a second stage, this unsaturated dinitrile is converted to an acid/ester nitrile of formula $R_3$OOC—[CH=CH]$_x$—$(CH_2)_{p,n}$—CN, in which $R_3$ is H or an alkyl radical comprising from 1 to 4 carbon atoms, x is 0 or 1 and "p,n" means that the index is either p or n, according to the route chosen during the first stage, which conversion is carried out either by oxidative cleavage of unsaturated dinitrile or by a cross metathesis reaction of the unsaturated dinitrile with an acrylate of formula $CH_2$=CH—$COOR_3$, and, in a third stage, the acid/ester nitrile is hydrogenated to give an ω-amino acid (ester) of formula COOR—$(CH_2)_q$—$CH_2NH_2$.

2. The process as claimed in claim 1, wherein during the first stage, the homometathesis of the fatty acid (ester) of formula $R_1$—CH=CH—$(CH_2)_p$—$COOR_2$ is first of all carried out and then the ammoniation of the fatty diacids/diesters obtained to an acid nitrile of formula HOOC—$(CH_2)_p$—CN by oxidative cleavage and, finally, in a third stage, the nitrile functional group is reduced by hydrogenation to give an amine functional group, in order to obtain the compound of formula ROOC—$(CH_2)_p$—$CH_2NH_2$.

3. The process as claimed in claim 1, wherein during the first stage, the homometathesis of the fatty acid (ester) of formula $R_1$—CH=CH—$(CH_2)_p$—$COOR_2$ is first of all carried out, in order to obtain the diacid/ester of formula $R_2$OOC—$(CH_2)_p$—CH=CH—$(CH_2)_p$—$COOR_2$, and then the ammoniation of the fatty diacids/diesters obtained is carried out, in order to obtain a fatty dinitrile, then, in a second stage, this dinitrile is converted to an acid/ester nitrile of formula $R_3$OOC—[CH=CH]—$(CH_2)_p$—CN by cross metathesis with the alkyl acrylate $CH_2$=CH—$COOR_3$ and, finally, in a third stage, the double bond and the nitrile functional group are simultaneously reduced by hydrogenation to give an amine, in order to obtain the compound of formula $R_3$OOC—$(CH_2)_{p+2}$—$CH_2NH_2$.

4. The process as claimed in claim 1, wherein during the first stage, the ammoniation of the fatty acid (ester) of formula $R_1$—CH=CH—$(CH_2)_p$—$COOR_2$ is first of all carried out, resulting in the corresponding nitrile, and then the conversion by homometathesis of the nitrile to give an unsaturated fatty dinitrile of formula NC—$(CH_2)_p$—CH=CH—$(CH_2)_p$—CN is carried out, then this dinitrile is converted to an acid nitrile of formula HOOC—$(CH_2)_p$—CN by oxidative cleavage and, finally, in a third stage, the nitrile functional group is reduced to an amine functional group by hydrogenation, in order to obtain the compound of formula HOOC—$(CH_2)_p$—$CH_2NH_2$.

5. The process as claimed in claim 1, wherein during the first stage, the ammoniation of the fatty acid (ester) of formula $R_1$—CH=CH—$(CH_2)_p$—$COOR_2$ is first of all carried out, resulting in the corresponding nitrile, and then the conversion by homometathesis of the nitrile to give an unsaturated fatty dinitrile of formula NC—$(CH_2)_p$—CH=CH—$(CH_2)_p$—CN is carried out, then, in a second stage, this dinitrile is converted to an acid/ester nitrile of formula $R_3$OOC—[CH=CH]—$(CH_2)_p$—CN by cross metathesis with the alkyl acrylate $CH_2$=CH—$COOR_3$ and, finally, in a third stage, the double bond and the nitrile functional group are simultaneously reduced by hydrogenation to give an amine, in order to obtain the compound of formula $R_3$OOC—$(CH_2)_{p+2}$—$CH_2NH_2$.

6. The process as claimed in claim 1, wherein during the first stage, the oxidation by fermentation of the fatty acid/ester of formula $R_1$—CH=CH—$(CH_2)_p$—$COOR_2$ is first of all carried out, in order to obtain the diacid/ester of formula HOOC—$(CH_2)_p$—CH=CH—$(CH_2)_n$—$COOR_2$, and then the ammoniation of the fatty diacids/diesters obtained is carried out, in order to obtain a fatty dinitrile of formula NC—$(CH_2)_p$—CH=CH—$(CH_2)_n$—CN, then, in a second stage, this dinitrile is converted to a mixture of two acid/ester nitriles of formulae HOOC—$(CH_2)_p$—CN and HOOC—$(CH_2)_n$—CN by oxidative cleavage and, finally, in a third stage, the nitrile functional group is reduced by hydrogenation to an amine functional group, in order to obtain a mixture of compounds of formulae HOOC—$(CH_2)_p$—$CH_2NH_2$ and HOOC—$(CH_2)_n$—$CH_2NH_2$.

7. The process as claimed in claim 1, wherein during the first stage, the oxidation by fermentation of the fatty acid/ester of formula $R_1$—CH=CH—$(CH_2)_p$—$COOR_2$ is first of all carried out, in order to obtain the diacid/ester of formula HOOC—$(CH_2)_p$—CH=CH—$(CH_2)_n$—$COOR_2$, and then the ammoniation of the fatty diacids/diesters obtained is carried out, in order to obtain a fatty dinitrile of formula NC—$(CH_2)_p$—CH=CH—$(CH_2)_n$—CN, then, in a second stage, this dinitrile is converted to a mixture of two acid/ester nitriles of formulae $R_3$OOC—[CH=CH]—$(CH_2)_p$—CN and $R_3$OOC—[CH=CH]—$(CH_2)_n$—CN by cross metathesis with the alkyl acrylate $CH_2$=CH—$COOR_3$ and, finally, in a third stage, the double bond and the nitrile functional group are simultaneously reduced by hydrogenation to give an amine, in order to obtain a mixture of compounds of formulae $R_3$OOC—$(CH_2)_{p+2}$—$CH_2NH_2$ and $R_3$OOC—$(CH_2)_{n+2}$—$CH_2NH_2$.

8. The process as claimed in claim 1, wherein the metatheses are carried out in the presence of a ruthenium-based catalyst.

9. The process as claimed in claim 1, wherein oxidation by fermentation is carried out by means of microorganisms comprising enzymes of Oxygenase type.

10. The process as claimed in claim 1, wherein the oxidative cleavage is carried out by ozonolysis.

11. The process as claimed in claim 1, wherein the cross metathesis reaction is carried out with methyl acrylate.

* * * * *